United States Patent
Ormerod et al.

(10) Patent No.: US 10,472,390 B2
(45) Date of Patent: Nov. 12, 2019

(54) REACTION PROCESS WITH MEMBRANE SEPARATION

(71) Applicant: VITO NV, Mol (BE)

(72) Inventors: Dominic Ormerod, Mol (BE); Anita Buekenhoudt, Mol (BE)

(73) Assignee: Vito NV, Mol (BE)

( * ) Notice: Subject to any disclaimer, the term of this patent is extended or adjusted under 35 U.S.C. 154(b) by 194 days.

(21) Appl. No.: 15/511,384

(22) PCT Filed: Sep. 17, 2015

(86) PCT No.: PCT/EP2015/071302
§ 371 (c)(1),
(2) Date: Mar. 15, 2017

(87) PCT Pub. No.: WO2016/042066
PCT Pub. Date: Mar. 24, 2016

(65) Prior Publication Data
US 2017/0260229 A1    Sep. 14, 2017

(30) Foreign Application Priority Data

Sep. 17, 2014    (EP) .................................... 14185205

(51) Int. Cl.
*C07K 1/34*    (2006.01)
*B01J 19/24*    (2006.01)
(Continued)

(52) U.S. Cl.
CPC ................ *C07K 1/34* (2013.01); *B01D 61/04* (2013.01); *B01D 61/10* (2013.01); *B01D 61/16* (2013.01);
(Continued)

(58) Field of Classification Search
CPC ....... C07K 1/34; B01J 19/002; B01J 19/2475; B01J 19/2465; B01J 8/006;
(Continued)

(56) References Cited

U.S. PATENT DOCUMENTS 4,754,089 A * 6/1988 Matson ...................... B01J 4/04
560/1
5,009,789 A * 4/1991 Helmer ................ B01D 61/145
210/195.2
(Continued)

FOREIGN PATENT DOCUMENTS

WO    WO 88/05444 A1    7/1988

OTHER PUBLICATIONS

International Search Report and Written Opinion of the International Searching Authority for International Application No. PCT/EP2015/071302, dated Jan. 1, 2016, in 9 pages.

*Primary Examiner* — Joseph W Drodge
(74) *Attorney, Agent, or Firm* — Knobbe, Martens, Olson & Bear, LLP

(57) ABSTRACT

Provided herein are processes for carrying out a chemical reaction of a substrate in a diluted reaction mixture. The processes include conducting the reaction mixture having reaction product and solvent to a filtration membrane which is permeable to the solvent but impermeable to the reaction product. Solvent which permeates the filtration membrane for dilution of the substrate feed is recycled.

13 Claims, 3 Drawing Sheets

(51) Int. Cl.
  *B01J 8/00* (2006.01)
  *B01D 61/04* (2006.01)
  *B01D 61/10* (2006.01)
  *B01D 61/16* (2006.01)
  *B01D 61/20* (2006.01)
  *B01J 19/00* (2006.01)
(52) U.S. Cl.
  CPC .............. *B01D 61/20* (2013.01); *B01J 8/006* (2013.01); *B01J 19/002* (2013.01); *B01J 19/2465* (2013.01); *B01J 19/2475* (2013.01); *B01J 2219/00245* (2013.01); *B01J 2219/00252* (2013.01); *B01J 2219/00259* (2013.01); *Y02P 20/582* (2015.11)
(58) Field of Classification Search
  CPC .... B01J 2219/00245; B01J 2219/00259; B01J 2219/00252; B01J 2219/00889; B01J 2219/00891; B01J 2219/00905; Y02P 20/582; C07D 267/00; B01D 61/145; B01D 61/022; B01D 61/025; B01D 61/142; B01D 61/147; B01D 61/12; B01D 61/027; B01D 2315/16; B01D 2311/263; B01D 11/028; B01D 11/0284; B01D 11/0288; B01D 11/0292; B01D 11/0488; B01D 11/0492; B01D 61/04; B01D 61/10; B01D 61/16; B01D 61/20; C12P 13/02; C07C 67/343

USPC .... 210/195.2, 511, 205, 206, 634, 638, 639, 210/651, 805; 422/608, 617, 618, 630, 422/622

See application file for complete search history.

(56) References Cited

U.S. PATENT DOCUMENTS

| | | | |
|---|---|---|---|
| 6,307,099 B1* | 10/2001 | Turner | B01J 8/06 562/412 |
| 10,214,499 B2* | 2/2019 | Buekenhoudt | B01D 61/027 |
| 2002/0082375 A1* | 6/2002 | Andrist | B01F 17/0028 526/317.1 |
| 2004/0211729 A1 | 10/2004 | Sunkara et al. | |
| 2006/0124547 A1 | 6/2006 | Allan | |
| 2008/0044324 A1* | 2/2008 | Ying | B01J 8/0214 422/211 |
| 2008/0103346 A1* | 5/2008 | Burdett | B01D 61/027 585/818 |
| 2010/0190965 A1 | 7/2010 | Yamaguchi et al. | |
| 2012/0071316 A1* | 3/2012 | Voss | B01D 61/027 502/21 |
| 2013/0146537 A1* | 6/2013 | Chilekar | B01D 61/246 210/644 |
| 2013/0266991 A1* | 10/2013 | Kanamori | B01D 61/16 435/99 |

* cited by examiner

REACTION PROCESS WITH MEMBRANE SEPARATION

CROSS-REFERENCE TO RELATED APPLICATIONS

This application is the U.S. National Phase under 35 U.S.C. § 371 of International Application PCT/EP2015/071302, filed Sep. 17, 2015, which claims priority to EP 14185205.3, filed Sep. 17, 2014.

FIELD OF THE INVENTION

The present invention relates to a process for carrying out a chemical reaction which requires for at least one reason the reaction of a substrate in diluted form, such as a cyclization reaction, a polymerization reaction, an enzymatic reaction showing substrate inhibition, or a reaction showing precipitation of the substrate or of the reactant.

BACKGROUND OF THE INVENTION

Industry is often faced with the problem that certain reactions must be carried out at low concentration and/or high dilution of one or more of the substrates, typically to avoid side reactions which may lead to the formation of unwanted side products.

Examples of reactions which are often performed at high dilution include cyclization reactions, such as intramolecular macrocyclization reactions for the production of active pharmaceutical ingredients. In such reactions, high substrate concentrations may favour the formation of intermolecular reactions instead of intramolecular reactions, which can lead to polymerization of the substrate in the reaction medium or to the occurrence of other unwanted side-reactions, thereby decreasing the yield to the desired product and the product purity.

Similar unwanted intermolecular side reactions have been observed in certain types of polymerization reactions, for example in the synthesis of cyclic polymers. Enzymatic reactions with substrate inhibition exemplify another type of reactions that are preferably carried out at high dilution of the substrate. Indeed, in such reactions a high substrate concentration may lead to a declining catalytic activity of the enzyme. Yet other types of reactions which favour low concentration of the substrate include reactions wherein high substrate concentrations lead to unwanted precipitation of one or more components within the reaction mixture.

Accordingly, certain reactions are preferably carried out at high dilution of the substrate in order to minimize the formation of unwanted side products. In particular in batch reactions, this requires the use of large amounts of solvent, as frequently used solvent dilution rates mount to 100-1000 L/mol of substrate to permit keeping substrate concentration sufficiently low. In other words, for the production of small quantities of an end product, often the use of large volumes of solvent and the use of large reactor volumes is required, thereby obtaining small reaction product yields per unit volume of reactor.

For a number of reactions, the total amount of solvent required for reaction may be reduced by using a so-called "fed-batch" process, wherein the substrate is gradually added to the reactor and in which the product(s) remain in the reactor until the end of the run. However, such process is only useful if the desired reaction products are stable in the reactor. However, it is not uncommon that the reaction is reversible, thus leading to a too high concentration of substrate which may result in the formation of unwanted side products.

US20040211729 discloses a process and system for recovering oligomers and/or acid catalyst from wash streams using filter membranes, wherein the product stream is removed via a settler. The preferred operation of the process is a batch operation, and in case of a continuous operation there is no recycling of retentate. In addition, the reaction is not performed in dilute conditions.

WO88/05444 discloses a process and system for separation of synthetic water soluble polymers, wherein the polymerization reaction is performed as a batch reaction and wherein the product stream is charged into a membrane unit with recirculation of the permeate obtained after filtration to the reactor.

Thus, there is a need for processes and systems suitable for carrying out reactions which require maintaining one or more of the substrates at a low concentration, more particularly which are equally suitable for reactions wherein the reaction product is not stable in the reactor.

SUMMARY OF THE INVENTION

It is an aim of the present invention to provide a process for carrying out a chemical reaction of a substrate in a diluted reaction mixture which, compared to a batch process, requires significantly less solvent for the same amount of reaction product. It is a further aim of the present invention to provide such processes which are suitable for carrying out reactions wherein the reaction product is unstable under the applied reaction conditions.

More particularly, provided herein is a continuous process for carrying out a chemical reaction of a substrate in a diluted reaction mixture comprising a solvent, the process comprising the steps of:
   (a) (simultaneously) adding a substrate feed and a solvent for diluting said substrate feed to form a reaction mixture in a reactor; and causing said substrate to form a reaction product in said reaction mixture;
   (b) discharging, from an outlet of the reactor, reaction mixture comprising reaction product and solvent;
   (c) conducting the reaction mixture discharged in step (b) to a filtration membrane, whereby the filtration membrane is permeable to the solvent and provided to be impermeable to the reaction product;
   (d) recycling solvent which permeates the filtration membrane for diluting said substrate feed in step (a); and
   (e) conducting the retentate from said filtration membrane to a reservoir other than said reactor, said retentate comprising reaction product.

In particular embodiments, the reaction is selected from the group consisting of a cyclization reaction, a polymerization reaction, an enzymatic reaction showing substrate inhibition, an enzymatic reaction showing product inhibition, a reaction showing precipitation of the substrate or of a co-reactant, and combinations thereof.

In certain embodiments, the substrate feed and said solvent (continuously) enter said reactor as separate streams which are mixed inside said reactor, and step (d) comprises continuously returning solvent which permeates the filtration membrane to said reactor.

In particular embodiments, said substrate feed and said solvent are mixed in a mixing vessel to form a diluted substrate feed which is continuously discharged from said mixing vessel to said reactor, wherein step (d) comprises continuously returning solvent which permeates the filtration membrane to said mixing vessel.

In certain embodiments, step (a) further includes mixing said substrate feed and solvent with one or more additional components selected from a catalyst and a co-reactant which is to be reacted with said substrate. In further embodiments, the substrate feed is continuously discharged from a substrate feed tank and said one or more additional components are continuously discharged from one or more feed tanks other than said substrate feed tank. In certain embodiments, the rejection of said filtration membrane is below 10% for one or more components selected from said co-reactant, said catalyst, and one or more side products.

In particular embodiments, step (c) comprises conducting the reaction mixture discharged in step (b) to a filtration loop feed tank; discharging reaction mixture from an outlet of said filtration loop feed tank; and conducting the reaction mixture to said filtration membrane; and step (e) comprises returning the retentate from said filtration membrane to said filtration loop feed tank.

In certain embodiments, the volume of solvent added in step (a) is at least 5 times the volume of substrate feed added in step (a).

In particular embodiments, at least 95% of the solvent added in step (a) is solvent from the permeate side of the filtration membrane.

In certain embodiments, said filtration membrane has a reaction product rejection of at least 90%.

In particular embodiments, said filtration membrane has a substrate rejection of at least 95%.

In certain embodiments, said filtration membrane is selected from the group consisting of a nanofiltration membrane, a microfiltration membrane, an ultrafiltration membrane, a reverse osmosis filtration membrane, and combinations thereof.

In particular embodiments, the temperature within the filtration loop and reaction vessel may be different. More particularly, the temperature within the filtration loop feed tank and the reaction vessel may be different. Most particularly, the temperature within the filtration loop feed tank may be lower than the temperature within the reaction vessel.

Further provided herein is a system for carrying out a chemical reaction of a substrate in a diluted reaction mixture comprising a solvent, comprising:
(i) a reactor (3) comprising:
  a first, second, and third inlet (7, 8, 9); and
  a reactor outlet (13);
(ii) a first feed tank (1) connected to said reactor (3) via said first inlet (7);
(iii) optionally, a second feed tank (2) connected to said reactor (3) via said second inlet (8);
(iv) a filtration loop feed tank (4) comprising:
  a first filtration loop feed tank inlet (10) which is connected to said reactor (3) via said reactor outlet (13);
  a second filtration loop feed tank inlet (11); and
  a filtration loop feed tank outlet (14); and
(v) a filtration membrane (5) configured for receiving a solution from said filtration loop feed tank outlet (14), said filtration membrane having a retentate side (15) and a permeate side (16), whereby the filtration membrane is further configured for returning the permeate to said reactor (3) via said third inlet (9), and for returning the retentate to said filtration loop feed tank (4) via said second filtration loop feed tank inlet (11).

In particular embodiments, said reactor (3) is a continuously stirred reactor.

Further provided herein is a system for carrying out a chemical reaction of a substrate in a diluted reaction mixture comprising a solvent, comprising:
(i) a reactor (3) comprising:
  a first and second inlet (7, 8); and
  a reactor outlet (13);
(ii) a mixing vessel (6) having an inlet (12) and connected to said reactor (3) via said first inlet (7);
(iii) a first feed tank (1) connected to said mixing vessel (6);
(iv) optionally, a second feed tank (2) connected to said reactor (3) via said second inlet (8)
(v) a filtration loop feed tank (4) comprising:
  a first filtration loop feed tank inlet (10) which is connected to said reactor (3) via said reactor outlet (13);
  a second filtration loop feed tank inlet (11); and
  a filtration loop feed tank outlet (14); and
(vi) a filtration membrane (5) configured for receiving a solution from said filtration loop feed tank outlet (14), said filtration membrane having a retentate side (15) and a permeate side (16), whereby the filtration membrane is further configured for returning the permeate to said mixing vessel (6) via said inlet (12), and for returning the retentate to said filtration loop feed tank (4) via said second filtration loop feed tank inlet (11).

In particular embodiments, said reactor (3) is a continuously stirred reactor.

The inventors have found that the processes and systems described herein allow for obtaining similar or increased reaction product yield and/or product purity compared to a batch process at high dilution, while providing a much lower Process Mass Intensity (PMI).

Accordingly, the present processes may assist the chemical industry in its efforts towards higher sustainability. The above and other characteristics, features and advantages of the concepts described herein will become apparent from the following detailed description, which illustrates, by way of example, the principles of the invention.

BRIEF DESCRIPTION OF THE DRAWINGS

The following description of the figures of specific embodiments of the methods and instruments described herein is merely exemplary in nature and is not intended to limit the present teachings, their application or uses. Throughout the drawings, corresponding reference numerals indicate like or corresponding parts and features.

Figure 1:
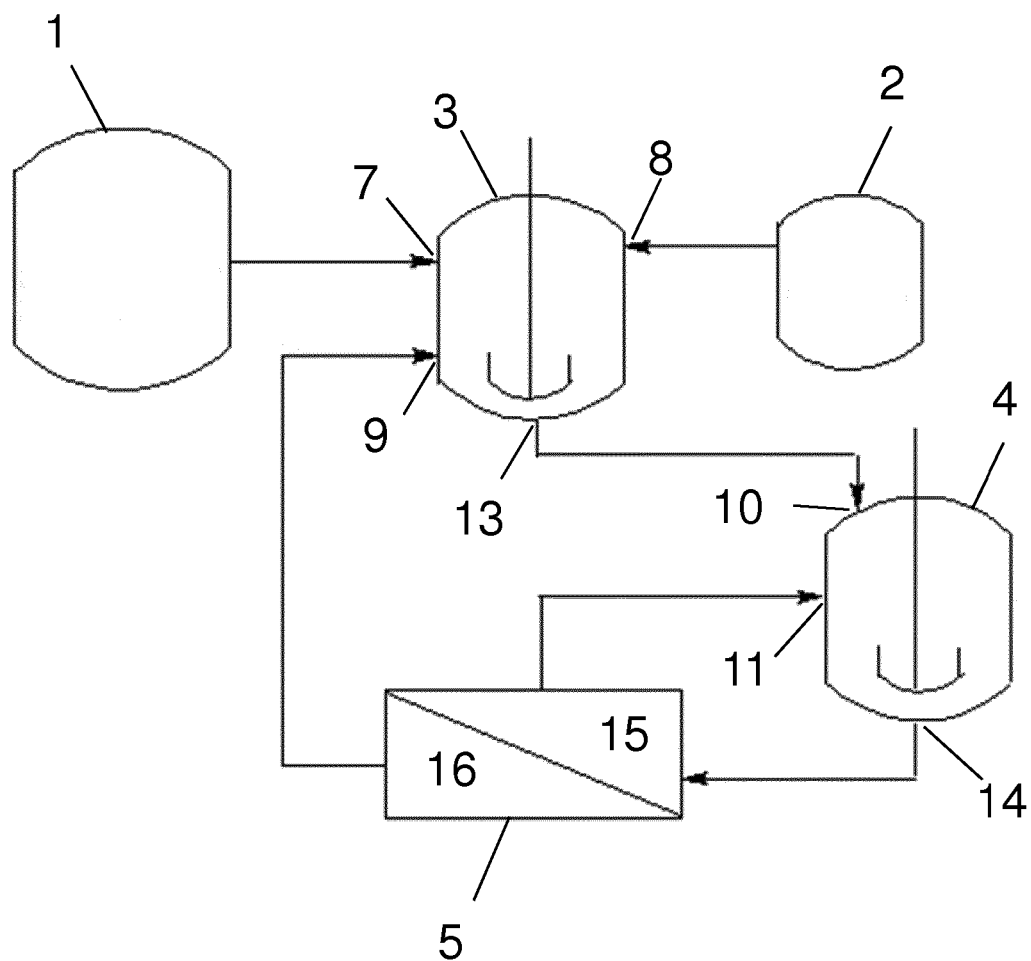
FIG. 1 Schematic illustration of a setup for a particular embodiment of the processes described herein, comprising a substrate feed tank (1), catalyst feed tank (2), reactor (3), filtration loop feed tank (4), and filtration membrane (5).

In the figures, the following numbering is used:
1—substrate feed tank; 2—catalyst feed tank; 3—reactor; 4—filtration loop feed tank; 5—filtration membrane; 6—mixing vessel; 7—first reactor inlet, 8—second reactor inlet, 9—third reactor inlet, 10—first filtration loop feed tank inlet, 11—second filtration loop feed tank inlet, 12—mixing vessel inlet; 13—reactor outlet; 14—filtration loop feed tank outlet; 15—retentate side; 16—permeate side; 17—acyclic peptide; 18—cyclic peptide.

DETAILED DESCRIPTION OF THE INVENTION

While potentially serving as a guide for understanding, any reference signs used herein and in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% less of and from the specified value, insofar such variations are appropriate to ensure one or more of the technical effects envisaged herein. It is to be understood that each value as used herein is itself also specifically, and preferably, disclosed. Typically, the term "about" should be read in this context.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure. The terms or definitions used herein are provided solely to aid in the understanding of the teachings provided herein.

In the context of the present invention, the terms "membrane" and "filtration membrane" are used interchangeably.

The term "constant volume diafiltration" as used herein refers to a continuous filtration process over a filtration membrane, wherein new liquid is added to the membrane on the retentate side at the same rate (volume per unit of time) as filtrate permeates through the membrane.

The term "cyclization reaction" as used herein refers to a chemical reaction whereby at least one ring is formed. A ring may be formed by one part of a molecule chemically condensing with another part of the same molecule, in which case the reaction is an intramolecular cyclization reaction. A ring may also be formed by a first part of a first molecule chemically connecting to or condensing with a first part of a second molecule, followed by a second part of the second molecule connecting to or condensing with a second part of the first molecule, in which case the reaction is an intermolecular cyclization reaction. In such intermolecular cyclization reaction, there may also be three or more molecules which form one single ring.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may.

Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

Provided herein are processes for carrying out a chemical reaction of a substrate in a diluted reaction mixture comprising a solvent. Examples of chemical reactions which often need to be carried out using a diluted substrate include, but are not limited to cyclization reactions, polymerization reactions, enzymatic reactions showing substrate inhibition, enzymatic reactions showing product inhibition, reactions showing precipitation of the substrate and/or of a co-reactant, and combinations thereof. For all these reactions, the present processes allow for performing the reaction at the required (high) dilution and lead to high yields in combination with low solvent use.

The processes provided herein are characterized in that they comprise conducting the reaction mixture comprising reaction product and solvent to a filtration membrane, whereby the filtration membrane is permeable to the solvent and provided to be impermeable to the reaction product. The present processes involve recycling of the solvent which permeates the filtration membrane and conducting the retentate from said filtration membrane to a reservoir other than the reactor.

More particularly, the processes described herein typically comprise the steps of:
  (a) adding a substrate feed and a solvent for diluting the substrate feed to a reactor; and causing the substrate to react to form a reaction product;
  (b) discharging, from an outlet of the reactor, reaction mixture comprising reaction product and solvent;
  (c) conducting the reaction mixture discharged in step (b) to a filtration membrane, whereby the filtration membrane is permeable to the solvent and provided to be impermeable to the reaction product;
  (d) recycling solvent which permeated the filtration membrane for diluting further substrate feed in step (a); and
  (e) conducting the retentate from said filtration membrane to a reservoir other than the reactor.

In preferred embodiments, the processes described herein are continuous processes. In these embodiments, the addition of substrate to the reactor and steps (b) to (e) are performed simultaneously with the reaction of the substrate in step (a). More particularly, the present processes may involve a continuous addition of substrate to the reactor, a continuous discharge of reaction mixture from the reactor, continuous filtration of the reaction mixture, and continuous recycling of the solvent as described above. The continuous addition, discharge, filtration, and solvent recycling can be constant (uninterrupted) or pulsed. The steps are preferably performed simultaneously. This will be explained further herein below.

In the processes described herein, a substrate is transformed into at least one reaction product of interest. Hereinafter, the term "reaction product" may refer to one or more reaction products of interest. In preferred embodiments of the process described herein, the substrate is an organic compound. In an embodiment, the molecule of the organic substrate contains a number of carbon and hydrogen atoms, yet other atoms, conventionally called "hetero atoms", such as oxygen, nitrogen, sulphur, may also be present. The organic compound may also have an ionic part, and may for instance be present as a salt. In particular embodiments, the substrate is subject to a cyclization reaction. Accordingly, the reaction product may be a cyclic molecule. In certain embodiments, the substrate may be subject to a polymerization reaction. Accordingly, the reaction product may be a polymer.

The substrate typically is a compound which is able to react in an intra- and/or an intermolecular pathway. An intramolecular chemical reaction is a reaction of a particular molecule with itself, such as in a cyclization reaction. An intermolecular reaction is a reaction of a molecule with another molecule. An intermolecular reaction may be a homo-intermolecular reaction, whereby the two molecules are of the same chemical compound. An intermolecular reaction may also be a hetero-intermolecular reaction, whereby the two molecules are of a different kind or chemical compound. In particular embodiments, the substrate may be able to react via a number of different competing pathways, wherein one (and only one) of the pathways leads to the desired reaction product. In the context of the present invention, the desired pathway may be favoured by carrying out the reaction in conditions of high dilution of the substrate.

In the processes described herein, the substrate is provided as a substrate feed, which is typically stored in a substrate feed tank. Thus, in particular embodiments, the substrate is provided to the reactor (3) from a substrate feed tank (1). The substrate feed may consist of the substrate as such, but is typically provided as a liquid comprising the substrate, more particularly as a solution of the substrate in a solvent or solvent mixture. The concentration of the substrate in the substrate feed typically is significantly higher than the desired substrate concentration during the reaction. Accordingly, the process described herein involves diluting the substrate feed with a solvent (see further). The precise concentration of the substrate in the substrate feed tank is not critical to the present process because the substrate concentration in the reactor will be determined by the amount of solvent added to the substrate feed before the reaction. In certain embodiments, the concentration of the substrate in the substrate feed is between 0.01 M and 10 M, more particularly between 0.02 and 5 M, 0.04 M and 2.0 M. In certain embodiments, the substrate feed may comprise additional non-solvent compounds, such as impurities. Preferably, the substrate is the main non-solvent compound present in the substrate feed, making up at least 50 wt %, 60 wt %, 70 wt %, 80 wt %, 85 wt %, 90 wt % or 95 wt % of the non-solvent compounds in the substrate feed.

In the processes described herein, the substrate feed and one or more solvents for diluting the substrate feed are added to a reactor to form reaction mixture. The substrate is then allowed to react, thus causing the substrate to form reaction product. Typically, the initial reaction mixture within the reactor will contain one or more solvents but no substrate. As substrate feed is added to the reactor, the substrate concentration will increase initially, followed by stabilization because the substrate reacts and reaction mixture is withdrawn from the reactor (see further).

The solvent(s) added to the substrate feed may be identical or different from any solvent already present in the substrate feed as stored in the substrate feed tank. For example, solvent for the substrate feed may be chosen such that they provide a high solubility and/or stability of the substrate, whereas the solvent for diluting the substrate may be chosen in function of the stability of the reaction product.

The relative volumes of substrate feed and additional solvent added to the reactor typically depends on the substrate concentration in the substrate feed, and the desired substrate concentration in the reaction mixture. The present process typically at least involves a 5-fold dilution of the substrate, preferably at least a 10-fold dilution. In certain embodiments, the volume of solvent added in step (a) is at least 10 times, and preferably at least 20 times, the volume of substrate feed added in step (a).

As indicated above, the processes described herein preferably are continuous processes. In such processes, the substrate feed and the solvent are continuously added to the reactor, as a constant (uninterrupted) stream or pulsed. The substrate feed and solvent are typically added to the reactor simultaneously. This facilitates obtaining a stable substrate concentration within the reactor throughout the process.

The present process is not limited to specific solvents. The choice of solvent to be used in the process may depend on factors such as the substrate type and type of filtration membrane used in the process. Examples of solvents suitable for use with the present invention include water, aromatics, alkanes, ketones, glycols, chlorinated solvents, esters, ethers, amines, nitriles, aldehydes, phenols, amides, carboxylic acids, alcohols, furans and dipolar aprotic solvents, and mixtures of two or more of the aforementioned solvents as well as mixtures of one or more of the aforementioned solvents with water.

Figure 2:
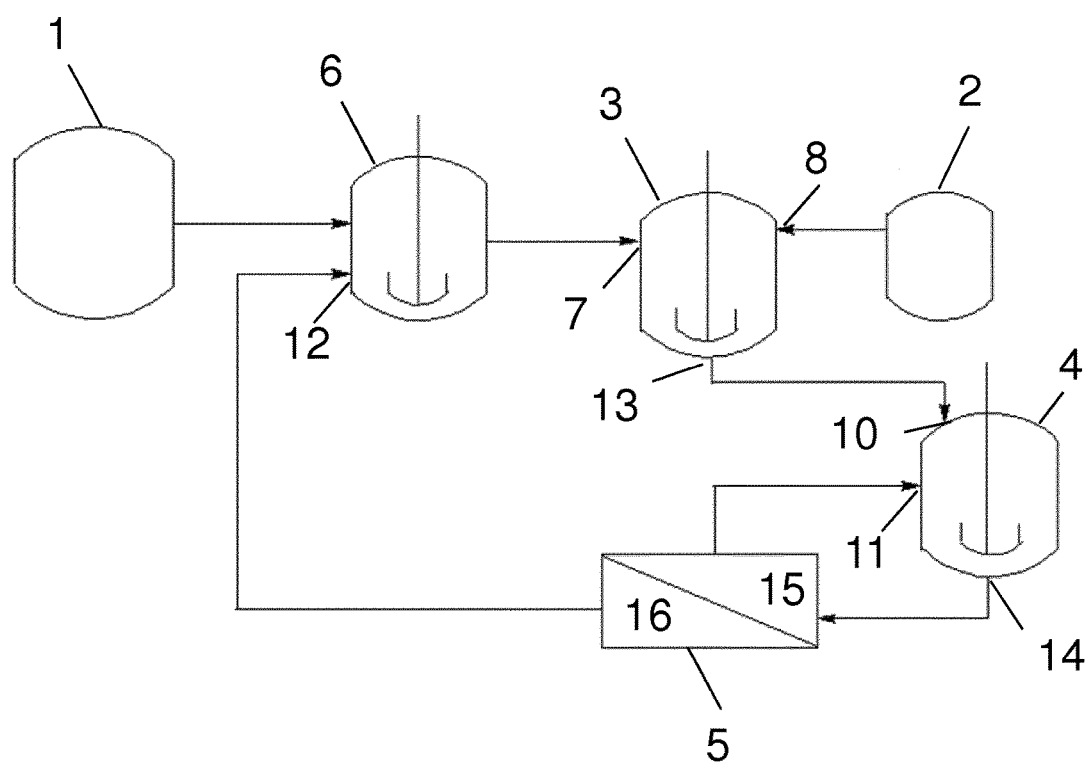
FIG. 2 Schematic illustration of a setup for a particular embodiment of the processes described herein, comprising a substrate feed tank (1), mixing vessel (6), catalyst feed tank (2), reactor (3), filtration loop feed tank (4), and filtration membrane (5).

In particular embodiments, the substrate feed and the solvent for diluting the substrate feed may enter the reactor (3) simultaneously as a single stream, via the same reactor inlet (7). In such embodiments, the substrate feed and the solvent are typically mixed in a dedicated mixing vessel (6) to form a diluted substrate feed, which then is continuously transferred from the mixing vessel to the reactor (3). A non-limiting example of a setup suitable for carrying out processes according to these embodiments is illustrated in FIG. 2. In other embodiments, the substrate feed and the solvent for diluting the substrate feed may enter the reactor (simultaneously) as a two separate streams, more particularly via two separate inlets (7, 9) of the reactor (3). Thus, in such embodiments, the substrate feed and the solvent are mixed inside the reactor. A non-limiting example of a setup suitable for carrying out processes according to these embodiments is illustrated in FIG. 1. The mixing of the substrate feed and solvent within the reactor eliminates the need of a dedicated mixing vessel (6) as described above. On the other hand, it may be more difficult to control the mixing inside the reactor compared to mixing inside a dedicated mixing vessel.

In preferred embodiments, the process is operated with an ongoing feed of fresh substrate from the substrate feed tank (1) to the reactor (3), optionally via the mixing vessel (6), such that the amount of substrate present in the reactor (3)

is replenished as it is consumed through reaction. In this way, the concentration of the substrate within the reactor is kept stable. The rate at which the substrate is consumed may be monitored during the process, or may be estimated based on previous measurements.

Upon or after diluting the substrate feed with solvent, the substrate may become exposed to conditions under which it may react. More particularly, once the diluted substrate and optional other reaction components are entered in the reactor, the substrate is caused to react to form a desired reaction product. Accordingly, the conditions in the reactor are chosen such as to enable such reaction. This may involve providing an appropriate reaction temperature and/or pressure inside the reactor, which may differ from reaction to reaction.

For certain reactions, it may be necessary to introduce other components in the reactor in addition to the substrate and one or more solvents. For example, the reaction may require the presence of one or more catalysts, and/or the substrate may need to react with a co-reactant, i.e. a reactant other than the substrate.

In certain embodiments, one or more additional components may already be provided in the substrate feed in the substrate feed tank (1). However, in some cases a substrate/co-reactant mixture may not be sufficiently stable for storage in a single feed tank.

Accordingly, in preferred embodiments, the additional components are not present in the substrate feed.

In particular embodiments, one or more additional components may initially be provided in the reactor. For example, at the beginning of the process, the reactor may be provided with a starting solvent and one or more catalysts. In such embodiments, the filtration membrane preferably has a high rejection (e.g. at least 90% and preferably at least 95%) for the reaction product, but a low rejection (e.g. at most 10% and preferably at most 5%) for the solvent and catalyst, and optionally also for unreacted substrate. This allows for the solvent, catalyst, and optionally unreacted substrate to return to the reactor for continuing the process. Preferably, the filtration loop feed tank and the rest of the filtration loop (such as the filtration membrane) are operated at conditions which prevent further reaction of the components of the reaction mixture, such as at a temperature which is sufficiently low to prevent further reaction of the components of the reaction mixture which is discharged from the reactor. Accordingly, the filtration loop is preferably operated at a temperature which is lower than the temperature within the reactor. In this way, the reaction substantially only occurs within the reactor.

Additionally or alternatively, one or more additional components may be provided in one or more feed tanks (2) other than the substrate feed tank (1). Accordingly, the substrate feed is then (continuously) discharged from a substrate feed tank (1), whereas the one or more additional components are (continuously) discharged from one or more feed tanks other than the substrate feed tank. If the process involves the use of two or more additional components, they may be provided in separate feed tanks or, if the mixture of the additional components is sufficiently stable, in the same feed tank.

Thus, in certain embodiments of the present processes, step (a) may further include mixing the substrate feed and solvent with one or more additional components selected from a catalyst and a reactant which is to be reacted with the substrate.

In certain embodiments, the substrate feed, the solvent(s) for diluting the substrate feed, and the one or more additional components may enter the reactor (3) as separate streams, which are mixed inside the reactor. The separate streams typically enter the reactor via separate inlets (7, 8, 9). However, it is envisaged that certain components may be mixed with each other prior to entering the reactor.

In particular embodiments, the one or more additional components may be mixed with the substrate feed and solvent in a dedicated mixing vessel. In certain embodiments, this may be the same mixing vessel (6) as used for mixing the substrate feed with the solvent(s) for diluting the substrate feed. However, for certain reactions, it may be preferred to dilute the substrate prior to addition of further components. In such embodiments, the substrate feed and solvent(s) for diluting the substrate feed are mixed first in a dedicated mixing vessel to form a diluted substrate feed, which is then mixed with the additional components in the reactor (3) or another dedicated mixing vessel. In certain embodiments, a dedicated mixing vessel may be provided for each of the one or more additional components.

In the present processes, reaction mixture is continuously discharged form an outlet (13) of the reactor (3). As the substrate is allowed to react to form reaction product as described above, the reaction mixture which is discharged comprises reaction product and solvent.

In certain embodiments, the reaction mixture which is discharged may also comprise other components, such as unreacted substrate, unreacted co-reactant, catalyst, and side products (i.e. end forms of the substrate other than the reaction product which is desired). Typically, the reaction conditions and process parameters will be chosen such that the presence of these components is minimized.

For example, the amount of unreacted substrate and optional co-reactants may be minimized by adjusting the rate (volume per unit of time) at which the reaction mixture is discharged from the reactor. A lower discharge speed means that the substrate and optional co-reactants have a longer residence time in the reactor, which allows for a higher fraction of the substrate to react. Furthermore, the fraction of unreacted substrate or co-reactant may be lowered by providing the substrate and co-reactant to the reactor in stoichiometric amounts.

As indicated above, the processes described herein preferably are continuous processes. In such processes, reaction mixture is continuously withdrawn from the reactor, as a constant (uninterrupted) stream or pulsed. Typically, the rate at which reaction mixture is discharged from the reactor is matched with the rate at which substrate feed and solvent are added to the reactor, thereby allowing the volume and composition of the reaction mixture to stabilize.

In certain embodiments, the reaction mixture which is discharged from the reactor may comprise small amounts of unreacted substrate and/or co-reactant, which may lead to the formation of unwanted side products. Additionally or alternatively, the reaction product may have a limited stability in the discharged reaction mixture, and may tend to react further to form unwanted side products. The formation of such unwanted side products may be prevented by cooling the reaction mixture. Accordingly, in particular embodiments, the step (b) of discharging reaction mixture from the reactor may further include cooling the reaction mixture which is discharged from the reactor. Accordingly, in certain embodiments, the temperature within filtration loop feed tank (and typically other components of the filtration loop such as the filtration membrane) may be different from the temperature within the reaction. More particularly, the temperature within the filtration loop feed tank may be lower than the temperature within the reaction.

In particular embodiments the temperature within the filtration loop feed tank may be at least 5° C., at least 10° C., or at least 20° C. lower than the temperature within the reaction.

In a further step (c) of the present processes, the reaction mixture which is discharged from the reactor is conducted to a filtration membrane, whereby the filtration membrane is permeable to the solvent and provided to be impermeable to the reaction product. Accordingly, the filtration membrane is able to separate or isolate the solvent(s) from the reaction product. A typical filtration membrane (5) has a permeate side (16) and a retentate side (15), as known in the art and illustrated in FIG. 1 and FIG. 2.

The use of filtration membranes for solvent recovery is less energy intensive than conventional solvent recovery techniques such as distillation, evaporation and crystallization. Moreover, these conventional techniques often are not compatible with continuous reactions as described herein, the reaction product (e.g. due to the use of high temperatures), and/or the reaction conditions used. Presently, filtration membranes are mainly used for purification of reaction products after reaction, whereas the present processes involve an in situ solvent recuperation.

The filtration membrane used in the present processes is impermeable to the reaction product. As used herein, a filtration membrane is considered "impermeable" to a specific component of a composition if the membrane rejection for that component is between 80% to 100%, i.e. 80% to 100% of the component remains present in the retentate upon filtration. However, for optimal results, it is preferred that the reaction product rejection is at least 90%, preferably at least 95%, more preferably at least 97%, and most preferably at least 99%.

The rejection of the membrane for the various components which may be present in the reaction mixture, such as the reaction product, substrate, catalyst(s), co-reactant(s), and side product(s), may be the same or different. More particularly, in particular embodiments, the filtration membrane may be selected such that it is further able to separate or isolate the solvent(s) from one or more other components which may be contained in the reaction mixture which is discharged from the reactor, such as unreacted substrate, catalyst(s), unreacted co-reactant(s), and/or side product. Accordingly, in certain embodiments, the filtration membrane may be impermeable to one or more components selected from the substrate, one or more catalysts used in the reaction, one or more co-reactants, and/or side product. In specific embodiments, the filtration membrane may be impermeable to the reaction product and to one or more side products. However, it is envisaged that in certain embodiments, the filtration membrane may be permeable to one or more of the components other than the reaction product. In certain embodiments, the rejection of the filtration membrane is below 10% for one or more components selected from the substrate, a catalyst (if used), and a co-reactant. In this way, the unreacted substrate, catalyst, and/or unreacted co-reactants may be returned to the reactor (optionally via a mixing vessel (6) as described above), where they are allowed to react to form the desired reaction product.

Thus, the filtration membrane may be permeable or impermeable to the substrate. In preferred embodiments, the filtration membrane is impermeable to the substrate. More particularly, the filtration membrane may have a substrate rejection of at least 75%, preferably at least 90%, preferably at least 95%, more preferably at least 97%, and most preferably at least 99%. In this way, it can be ensured that the permeate is essentially free from substrate, which facilitates keeping the substrate concentration within the reactor (3) and/or mixing vessel (6) constant.

However, the process will typically be carried out such that the reaction mixture which is discharged from the reactor in step (b) contains (almost) no unreacted substrate. Under such conditions, the permeate of the filtration membrane will be essentially free from substrate, even if the filtration membrane is permeable to the substrate.

In the present processes, the reaction mixture which is discharged from the reactor may be conducted to the filtration membrane directly or indirectly.

In particular embodiments, the reaction mixture is conducted to the filtration membrane in an indirect manner, for example as illustrated in FIG. 1 and FIG. 2. More particularly, the reaction mixture which is discharged from the reactor (3) via a reactor outlet (13) may first be conducted to a filtration loop feed tank (4), and mixed with the content of that tank. In such embodiments, content from the filtration loop feed tank (which includes reaction mixture) is discharged from the filtration loop feed tank (4) via a filtration loop feed tank outlet (14) and conducted to the filtration membrane (5).

The filtration loop feed tank can be used for the initial storage of solvent at the beginning of the reaction. Accordingly, the filtration loop feed tank provides a buffer for starting up the reaction and for ensuring the continuity of the reaction. Additionally or alternatively, the filtration loop feed tank may be used for accumulating the reaction product (see further).

Typically, the reaction mixture is not subject to any other filtration before it is conducted to the filtration membrane, be it directly or indirectly as described above. Accordingly, if the reaction mixture which is discharged from the reactor comprises other components than solvent and reaction product, these components are also conducted to the filtration membrane. Such other components may comprise one or more components selected from side products, unreacted substrate, unreacted co-reactant, and catalyst. Thus, in particular embodiments, the reaction mixture which is discharged from the reactor is transferred in its entirety, be it directly or indirectly as described above, to said filtration membrane. In preferred embodiments, the present processes involve the use of a single filtration membrane, i.e. the reaction mixture or permeate of the filtration membrane is not conducted to a second filtration membrane. However, this does not exclude further purification of the reaction product upon termination of the process.

Typically, the filtration will be operated in diafiltration mode. The latter involves a liquid filtration technique in which a feed liquid containing at least two compounds, i.e. the solvent and a reaction product, is contacted with a membrane and pressurised to force (a fraction of) the liquid to pass through the membrane. In the present processes, the filtration membrane has a high rejection for the reaction product, and a low rejection for the solvent. During filtration, fresh feed is supplemented to the feed side of the membrane to make up for the liquid permeating through the membrane, so as to be able to work at constant feed volume. The filtration membrane may further be operated in cross-flow filtration mode. In such mode, the liquid permeating the membrane is supplied in a direction parallel to the membrane, as this ensures a sufficient degree of turbulence at the membrane surface. However, it is envisaged that in certain embodiments, the filtration membrane may be operated in a dead-end filtration mode where the liquid permeating the membrane is supplied in a direction perpendicular to the membrane.

The filtration membrane may be made from a wide variety of materials and a wide variety of filtration membranes with varying cut-off values may be used. With cut-off or cut-off value is thereby meant the molecular mass of a molecule of which 90% is rejected by the membrane. The filtration membrane will be selected by the skilled person taking into account the nature of the solvent, substrate, or other reaction components the membrane is intended to reject.

Depending on the nature of the reaction, substrate, reactants and solvent involved, the membrane may be an ultrafiltration membrane with a typical cut-off ranging from 2 kDA to 500 kDa, or a microfiltration membrane with a typical cut-off for molecular weights above 500 kDa as probably more suitable in the case of enzymatic reactions or polymerization reactions. For reactions involving smaller molecules, for example macrocyclization reactions, the membrane will more probably be a nanofiltration membrane with typical cut-off values ranging from 200 Da to 2 kDa or even a reverse osmosis membrane with a typical cut-off of below 200 Da.

The filtration membrane is typically chosen such that the membrane rejection, cut-off and permeate flux meet the requirements imposed by the process and by the substrate, solvent and reaction product involved in the process. The filtration membrane is preferably chosen such that it shows a minimal risk to reacting with the components contained in the mixtures to which they are exposed, and to degradation of the components in the mixtures to which they are exposed, as well as a minimal risk to swelling as this may alter the flux through the membrane and their rejection properties. Thereby the membrane is preferably chosen such that it shows a stability of several months to several years in contact with the selected reaction solvent.

Suitable materials for use as filtration membrane in the device of this invention include polymeric or ceramic materials. Preferred materials include those polymeric materials suitable for fabricating microfiltration, ultrafiltration, nanofiltration or reverse osmosis membranes, including but not limited to polyethylene (PE), polypropylene (PP), polytetrafluoroethylene (PTFE), polyvinylidene difluoride (PVDF), polysulfone (PSf), polyethersulfone (PES), polyacrylonitrile (PAN), polyamide (PA), polyimide (PI), polyetherimide (PEI), polyamideimide (PAI), cellulose acetate (CA), polyaniline (PAn), polybenzimidazole (PBI), polyetheretherketone (PEEK), and combinations and mixtures thereof.

In certain embodiments, the filtration membrane may comprise a support which is provided with a (thin) selectively permeable top layer, wherein the latter may be formed from or comprises one or more polymers selected from but not limited to (modified) polysiloxane based elastomers, including polydimethylsiloxane (PDMS) based elastomers, ethylene-propylene-diene (EPDM) based elastomers, polynorbornene based elastomers, polyoctenamer based elastomers, polyurethane (PU) based elastomers, butadiene and nitrile butadiene rubber based elastomers, natural rubber and butyl rubber based elastomers, polychloroprene (Neoprene) based elastomers, epichlorohydrin elastomers, polyacrylate elastomers, polyvinylidene difluoride (PVDF) based elastomers, polyethylene, polypropylene, polytetrafluoroethylene (PTFE), polyamide, polyetherblock amides (PEBAX), poly(1-trimethylsilyl-1-propyne) (PTMSP) and other polyacetylenes, polyamide, polyaniline, polypyrrole, and combinations and mixtures thereof.

Techniques for the manufacture of polymeric membranes are known in the art, and include phase-inversion, sintering, stretching, track etching, template leaching, interfacial polymerisation, solvent casting, dip-coating, spin-coating and spray-coating. Membranes may be cross-linked or otherwise treated so as to improve their stability in the reaction solvents.

Other specific examples of suitable membrane materials include those produced from inorganic materials, for example silicon carbide, silicon oxide, zirconium oxide, titanium oxide, zeolites, and combinations or mixtures thereof, prepared using any technique known to those skilled in the art, such as e.g. sintering, leaching, hydrothermal or sol-gel processing.

The membrane used in the present invention may also comprise a polymer membrane with dispersed organic or inorganic particles in the form of powdered solids (mixed matrix membranes). The powdered solids will usually be present at amounts up to 20 wt % of the polymer membrane and include carbon molecular sieve particles, zeolites, and metal oxides, such as titanium dioxide, zirconium oxide, zinc oxide and silicon dioxide. Mixed metal oxides such as mixtures of cerium, zirconium, and magnesium oxides may also be used. Preferably the matrix particles have a number average diameter of less than 1.0 micron, more preferably less than 0.1 micron, and most preferably less than 0.01 micron.

These mixed-matrix membranes may be made by any technique known from the art, including sintering, stretching, track etching, template leaching, interfacial polymerisation or phase inversion. The polymers in the membranes may be cross-linked, or the membranes may otherwise be treated so as to improve their stability in the reaction solvents.

The membrane used in the present invention may also comprise a ceramic (or inorganic) membrane grafted on the outer surface, or on the complete pore surface, prepared using any grafting technique known to those skilled in the art, such as e.g. silanation, phosphonic acid grafting or Grignard grafting. Alternatively, the membrane may comprise a hybrid organic-inorganic material prepared by using e.g. sol-gel techniques starting from adapted metal oxide precursors, as known by those skilled in the art.

As indicated above, the processes described herein preferably are continuous processes. In such processes, reaction mixture (or filtration loop feed tank content) is continuously conducted over the filtration membrane, as a constant (uninterrupted) stream or pulsed. Typically, the rate at which solvent from the reaction mixture (or the content of the filtration loop feed tank) permeates through the membrane is matched with the rate at which reaction mixture is discharged from the reactor, and the rate at which substrate feed and solvent are added to the reactor. In preferred embodiments, the rate of these streams does not differ more than 5%, preferably not more than 1%.

As described above, the filtration membrane separates or isolates the solvent from the reaction product and optionally other components contained in the reaction mixture. More particularly, the permeate of the filtration membrane comprises (most of) the solvent, whereas the retentate comprises (most of) the reaction product. In the present processes, the solvent which permeates the filtration membrane from the permeate side is recycled (continuously) for diluting further substrate feed in step (a) as described above. This allows for minimizing solvent consumption and waste. In preferred embodiments, at least 95% of the solvent which is added in step (a) is solvent from the permeate side of the filtration membrane, more preferably at least 99%.

More particularly, in a step (d) of the present processes, the solvent which permeates the filtration membrane is recycled for diluting further substrate feed in step (a). More particularly this implies that the solvent from the permeate side of the filtration membrane is guided (directly or indirectly) to the inlet of the reactor.

In embodiments wherein the substrate is mixed with the solvent in a dedicated mixing vessel (6), step (d) comprises (continuously) returning solvent which permeated the filtration membrane to the mixing vessel (6). The solvent which is returned to the reactor (3) replenishes reaction mixture which is discharged from the reactor in step (b), and assists in achieving the envisaged substrate dilution in the reactor (3).

Similarly, in embodiments wherein the substrate is mixed with the solvent in the reactor (3), step (d) comprises (continuously) returning solvent which permeated the filtration membrane to the reactor (3). The solvent which is returned to the mixing vessel (6) replenishes reaction mixture which is discharged from the mixing vessel to the reactor (3), and assists in achieving the envisaged substrate dilution in the mixing vessel (6).

As indicated above, the processes described herein preferably are continuous processes. In such processes, solvent which has permeated is continuously recycled, and returned to the reactor (3) or mixing vessel (6) as a constant (uninterrupted) stream or pulsed. The rate at which solvent is returned to the reactor or mixing vessel is typically matched with the rate at which substrate feed is added to the reactor or mixing vessel, the rate at which reaction mixture is discharged from the reactor, and the rate at which reaction mixture permeates through the filtration membrane.

As described above, the filtration membrane (5) allows for separating the reaction product from the solvent(s), wherein the permeate contains (most of) the solvent, and the retentate comprises (most of) the reaction product. In the processes described herein, the retentate (comprising reaction product and optionally other components such as side product) is not returned to the reactor (3), but accumulated in a reservoir other than the reactor. In this way, it can be ensured that the reaction product does not react further to form unwanted side products. Accordingly, in the present processes, the retentate from the filtration membrane is conducted to a reservoir other than the reactor.

In embodiments involving the use of a filtration loop feed tank, the retentate of the filtration membrane the filtration loop feed tank may function as the reservoir wherein the reaction product is accumulated. Accordingly, in certain embodiments, step (e) of the present processes may comprise returning the retentate from the filtration membrane to the filtration loop feed tank. Thus, the filtration loop feed tank may not only provide a reservoir for the solvent, but can also provide a reservoir for accumulating the reaction product. This allows for performing the present processes using a relatively simple setup. Accumulating the reaction product in the filtration loop feed tank may further facilitate additional processing of the reaction product, if needed. Such processing may include washing the reaction product with pure solvent to remove impurities, performing a solvent switch such that the product is provided in a solvent suitable for a further purification step.

The processes described herein may be terminated once the substrate feed is exhausted, or more generally once a specific amount of substrate feed, catalyst, and/or co-reactant is consumed. From that point on, the addition of new substrate feed may be stopped, but the loop of discharging reaction mixture, filtration, and solvent reuse may be continued for a while, in order to increase the process yields by allowing the reaction to complete and by collecting as much reaction product as possible.

The present processes allow for performing a chemical reaction under high dilution on the substrate to be reacted. However, unlike corresponding batch processes wherein the reaction product is typically obtained in a highly diluted form, the reaction product obtained in the present processes is in a concentrated form, which significantly facilitates purification and/or further use of the reaction products. Thus, on termination of the process, the reaction products may be subjected to classical isolation and/or purification procedures or, depending on the constraints of potential following synthetic steps, used directly in a following reaction. In particular embodiments, the present processes may comprise the step (f) of purifying the reaction product which has accumulated in the reservoir as described above. Typically, step (f) is not carried out simultaneously with the other steps (a) to (e), but upon termination of these steps. The purification of the reaction product typically involves separating the reaction product from one or more impurities such as side products, substrate, co-reactant, and/or catalyst. Purification may involve filtration, distillation, liquid-liquid extraction, or other separation techniques known in the art.

Further provided herein are systems for carrying out a chemical reaction of a substrate in a diluted reaction mixture comprising a solvent. Examples of such systems are illustrated in FIG. 1 and FIG. 2. More particularly, the systems are suitable for carrying out the processes as described herein comprise a feed tank (1) for containing a substrate feed, as such or in a solvent solution. The feed tank (1) may be connected to a reactor (3) via a first inlet (7) (FIG. 1), or to a mixing vessel (6) which is connected to the reactor (3) via the first inlet (7) (FIG. 2). The term "connected" as used herein refers to a connection between two components of a system which allows a solution to flow from one component to the other. The reactor (3), wherein the reaction is allowed to take place, is further connected via an outlet (13) thereof to a filtration loop feed tank (4) via an inlet (10) thereof. The filtration loop feed tank (4) is further connected via an outlet (14) to a filtration membrane as described herein, having a retentate side (15) and a permeate side (16). The retentate is returned to the filtration loop feed tank (4) via an inlet (11) thereof, whereas the filtrate (solvent) is returned to the reactor (3) or to the mixing vessel (6) via an inlet (9, 12). Optionally, the systems may comprise further feed tanks (2) connected to the reactor (3) and/or mixing vessel (6) for containing catalysts and/or co-reactants.

In the systems envisaged herein the term "reactor" is used to describe a vessel wherein the substrate is allowed to react to form reaction product. In particular embodiments, this implies that the reaction vessel is configured to measure, monitor and/or manage (control) the conditions, such as pressure and/or temperature, inside the reactor as to enable such reaction.

In certain embodiments, the system may comprise:
(i) a reactor (3) comprising:
   at least a first and second (two or more of 7, 8, 9); and
   a reactor outlet (13);
(ii) a first feed tank (1) connected to said reactor (3) via said first inlet (7);
(iii) optionally, a second feed tank (2) connected to said reactor (3) via said second inlet (8)
(iv) a filtration loop feed tank (4) comprising:
   a first filtration loop feed tank inlet (10) which is connected to said reactor (3) via said reactor outlet (13);
   a second filtration loop feed tank inlet (11); and
   a filtration loop feed tank outlet (14); and
(v) a filtration membrane (5) configured for receiving a solution from said filtration loop feed tank outlet (14), said filtration membrane having a retentate side and a permeate side, whereby the filtration membrane is further configured for returning the permeate to said mixing vessel (6) via said inlet (12), and for returning the retentate to said filtration loop feed tank (4) via said second filtration loop feed tank inlet (11).

In particular embodiments, the system comprises two feed tanks, whereby the reactor is connected to a first feed tank via a first inlet (7) and to a second feed tank via a second inlet (8). In particular embodiments, the system comprises a third inlet (9) connected to the permeate side (16) of the filtration membrane (5).

In certain embodiments, the system may comprise a mixing vessel (6), which allows for diluting the substrate feed with solvent before the substrate feed enters the reactor (3). In such embodiments, the system may comprise:
 (i) a reactor (3) comprising:
   at least a first and second inlet (7, 8); and
   a reactor outlet (13);
 (ii) a mixing vessel (6) having an inlet (12) and connected to said reactor (3) via said first inlet (7);
 (iii) a first feed tank (1) connected to said mixing vessel (6);
 (iv) optionally, a second feed tank (2) connected to said reactor (3) via said second inlet (8);
 (v) a filtration loop feed tank 4 comprising:
   a first filtration loop feed tank inlet (10) which is connected to said reactor (3) via said reactor outlet (13);
   a second filtration loop feed tank inlet (11); and
   a filtration loop feed tank outlet (14);
 and
 (vi) a filtration membrane (5) configured for receiving a solution from said filtration loop feed tank outlet (14), said filtration membrane having a retentate side and a permeate side, whereby the filtration membrane is further configured for returning the permeate to said mixing vessel (6) via said inlet (12), and for returning the retentate to said filtration loop feed tank (4) via said second filtration loop feed tank inlet (11).

In particular embodiments, the system comprises two feed tanks, whereby the reactor is connected to a first feed tank via a first inlet (7) and to a second feed tank via a second inlet (8). In particular embodiments, the reactor comprises only a first and a second inlet connected to a feed tank. In particular embodiments, the system is configured to ensure that the first and second inlet connected to a feed tank are opened simultaneously.

In particular embodiments, the system comprises at least three inlets, one of which (9) is connected to the permeate side (16) of the filtration membrane (5).

In certain embodiments, the system may comprise means for adjusting the rate at which reaction mixture is discharged from the reactor (3) or filtration loop feed tank (4) and the substrate addition rate, in function of the membrane flux. The rate at which the reaction mixture is discharged from the reactor (3) or filtration loop feed tank (4) is determined by the membrane flux, as the filtration system is filled by constant volume diafiltration from the reactor or filtration loop feed tank. Thus, the membrane flux determines the rate at which reaction mixture is removed from the reaction vessel, and therefore also determines the rate at which the reaction needs to occur. Variation of the membrane flux can e.g. be achieved by altering the membrane and filtration parameters (membrane surface area, pressure etc.).

Examples of reactors suitable for use in the present systems may vary widely in nature and include conventional batch reactors as well as continuously stirred reactors, flow-reactors or micro-reactors. The reactors are typically provided with mixing means for ensuring a sufficient homogeneity of the reaction mixture contained in the reactor. The mixing means may further be used for mixing the substrate feed with solvent. Also the mixing vessel and filtration loop feed tank are typically provided with suitable mixing means.

To effectuate the liquid flows between the various components of the system, pressure may be used as a driving force, as is conventionally applied in microfiltration, ultrafiltration, nanofiltration, and reverse osmosis. Typically, this is obtained using pumps, as is known in the art.

EXAMPLES

The following examples are provided for the purpose of illustrating the claimed methods and applications and by no means are meant and in no way should be interpreted to limit the scope of the present invention.

Peptide Cyclization

Figure 3:
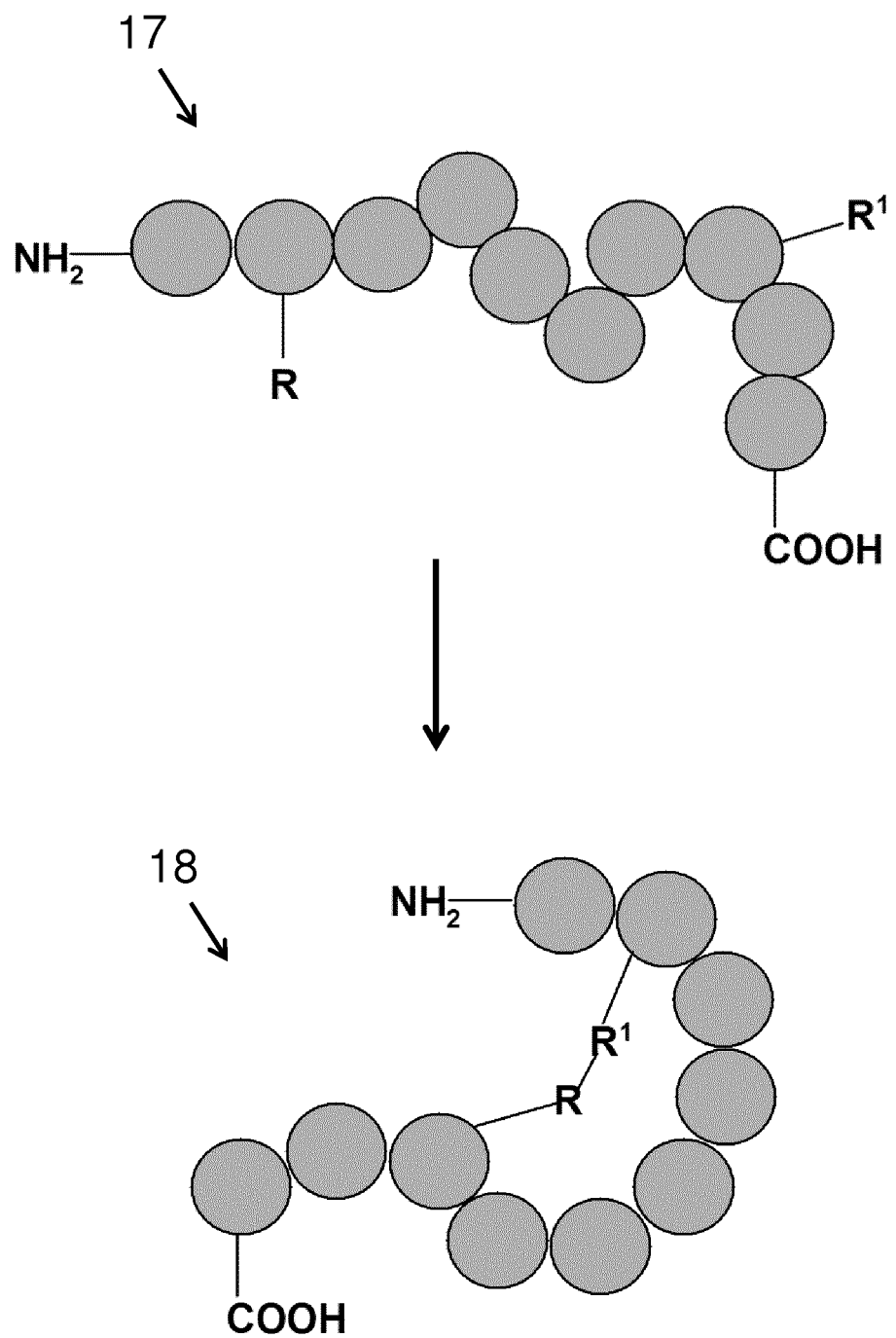
FIG. 3 Illustration of a peptide cyclization involving the internal reaction of two functional groups R and $R^1$ of an acyclic peptide (17) to form a cyclic peptide (18).

The processes described herein can be used for performing a variety of reactions, including peptide cyclization. A general peptide cyclization reaction via the internal reaction between two functional groups R and $R^1$ of an acyclic peptide substrate (17) to form a cyclic peptide reaction product (18) is illustrated in FIG. 3.

A cyclization reaction was performed using a setup as shown in FIG. 1. A summary of the components within each of the parts of the setup at the beginning of the process is provided in Table 1.

A substrate feed solution (a concentrated solution of acyclic peptide (17)) is provided in a substrate feed tank (1). A reagent or catalyst solution in a suitable solvent is provided in a separate feed tank (2). The substrate feed solution and reagent or catalyst solution are added continuously and simultaneously to the reactor (3) via first (7) and second (8) reactor inlets, respectively. The reactor (3) initially comprises a solvent or solvent mixture, to form a dilute reaction mixture comprising acyclic peptide. As the reaction proceeds, reaction mixture comprising reaction product (18) is removed continuously from the reactor (3) via a reactor outlet (13) and entered to a filtration loop feed tank (4) via a filtration loop feed tank inlet (10). The filtration loop feed tank (4) initially only contains solvent or solvent mixture. The solution contained in the filtration loop feed tank (4) is subjected continuously to constant volume diafiltration over a filtration membrane (5) having a retentate side (15) and a permeate side (16), using the solution in the reactor (3) as the diafiltration solution. The retentate (comprising cyclic peptide product (18)) is returned to the filtration loop feed tank (4), whereas the permeate (solvent) is returned to the reactor (3) via a third reactor inlet (9). The permeate addition rate to the reactor (3) is matched with the substrate feed addition, such that a constant dilution of the substrate in the reactor (3) is obtained.

In practice, it is sufficient to measure the membrane flux for the first 200 mL of permeate. Based on the measured flux, the rate at which the substrate feed and reagent/catalyst (iodine) solution are added can be determined.

A suitable membrane is used as a filtration membrane. Rejection of the acyclic peptide starting material (17) and the cyclic peptide product (18) over the ceramic membrane used were both found to be about ≥95%. The high rejection leads to an accumulation of the cyclic peptide product in the filtration loop feed tank (4) as the reaction proceeds.

The results using this process are summarized in Table 2. The cyclic peptide yield and acyclic peptide conversion (as determined via ultra performance liquid chromatography-UPLC) obtained via the process described herein (Entries 5-10) was found to be comparable to the values obtained from a corresponding batch reaction (Entry 1).

TABLE 1

Overview of the initial components within each part of the setup for performing a peptide cyclization reaction

| Setup part | Component |
| --- | --- |
| Substrate feed tank (1) | Acyclic peptide |
|  | solvent |
| Feed tank (2) | Reagent or catalyst |
|  | solvent |
| Reactor (3) | solvent |
|  | solvent |
| Filtration loop feed tank (4) | solvent |

TABLE 2

Cyclization of 1 to 2

| Entry | Yield (%) | Conversion (%) | Yield/conversion (%) | Reduction of solvent load (%) | PMI |
| --- | --- | --- | --- | --- | --- |
| 1 (batch) | 70.6 | 83.9 | 84.1 | 0 | 1703 |
| 5 | 42.3 | 49.8 | 85.0 | 63 | 1041 |
| 6 | 66.9 | 75.3 | 88.8 | 74 | 473 |
| 7 | 78.8 | 90.6 | 87.0 | 74 | 401 |
| 8 | 44.5 | 77.0 | 58.0 | 74 | 634 |
| 9 | 82.7 | 100 | 99 | 74 | 392 |
| 10 | 81.4 | 100 | 99 | 59 | 623.3 |

It is an aim of the present invention to provide a process for carrying out a chemical reaction of a substrate in a diluted reaction mixture which, compared to a batch process, requires significantly less solvent for the same amount of reaction product. A suitable metric for this is Process Mass Intensity (PMI) (see Jimenez-Gonzalez C et al., *Org. Process Res. Dev.* 2011, 15, 912) as it takes into account all input materials in the reaction and is recommended by the ACS green chemistry institute pharmaceutical roundtable. PMI is defined as the ratio of the total mass (reagents, solvent, etc.) in a process or process step versus the mass of reaction product obtained in that process or process step.

The PMI obtained for each of the experiments is included in Table 2. When comparing entry 1 (batch process) with entries 5-9 (reaction via the continuous process described herein) it is clear that the processes described herein require considerably less solvent than the corresponding batch processes.

Entry 5 shows the results of an process which is not optimized. Although the process allows for a reduction of solvent load of about 63%, the conversion of acyclic peptide and yield of and cyclic peptide is reduced in direct comparison with a batch reaction (Table 2 Entry 1). The reduced yield and conversion can be attributed to the fact that once the reaction mixture is removed from the mixer/reaction vessel very little or no further reaction occurs. Accordingly, a suboptimal yield is obtained if the cyclization to cyclic peptide is not complete before the reaction mixture is discharged from the reaction vessel.

The rate at which the reaction mixture is discharged from the reaction vessel is determined by the membrane flux, as the filtration system is filled by constant volume diafiltration from the reaction vessel. Thus, the membrane flux determines the rate at which reaction mixture is removed from the reaction vessel, and therefore also determines the rate at which the reaction needs to occur. Variation of the membrane flux can be achieved by altering the membrane parameters (surface area, pressure etc.). The rate at which the reaction mixture can be removed from the reaction vessel with sufficient conversion of the substrate (17) is determined by the reaction speed, which can be influenced by altering the reaction parameters.

In the present experiments the rate of cyclization was increased by increasing the mole equivalents of reagent used from two (as used in Table 2 entry 5) to three (Table 2 entries 6 to 9). Further measures to force the conversion to completion included adding some reagent to the mixer/reaction tank before the addition of acyclic peptide was started (Table 2 entry 7) and warming of this tank to 5° C. above the usual temperature (Table 2 entry 8), with mixed success. Complete conversion was eventually achieved by adding three equivalents of iodine as catalyst to the reaction vessel concomitantly with the addition of acyclic peptide. It was further found that better results were obtained with a smooth continuous addition of catalyst, compared to intermittent addition of catalyst.

Preparation of 1-desamino-8-D-arginine 1-desamino-8-D-arginine is represented by formula (I):

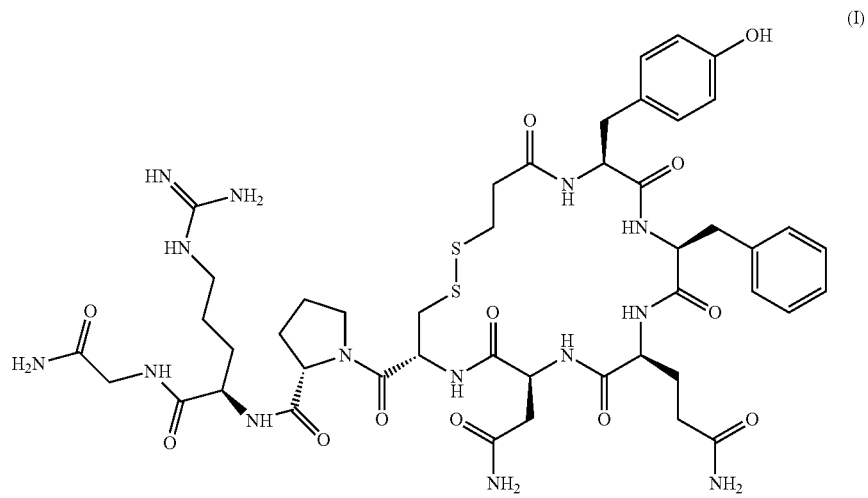 [SMILES: N=C(N)NCCC[C@@H](NC(=O)[C@@H]1CCCN1C(=O)[C@@H]1CSSCCC(=O)N[C@@H](Cc2ccc(O)cc2)C(=O)N[C@@H](Cc2ccccc2)C(=O)N[C@@H](CCC(N)=O)C(=O)N[C@@H](CC(N)=O)C(=O)N1)C(=O)NCC(N)=O]

1-desamino-8-D-arginine can be prepared via the cyclization of the acyclic nonapeptide (1-9)NH$_2$DDAVP (NH$_2$-Tyr-Phe-Gln-Asn-Cys-Pro-D-Arg-Gly-NH$_2$) under highly dilute conditions. The cyclization reaction is an oxidative process involving the formation of a sulphide bridge. An example of a conventional batch process for the synthesis of 1-desamino-8-D-arginine is described in U.S. Pat. No. 5,674,850. The batch process described therein requires large amounts of solvent (water and acetic acid) relative to the amount of reaction product.

The inventors have prepared 1-desamino-8-D-arginine via a particular embodiment of the processes described herein. As the substrate, (1-9)NH$_2$DDAVP was used with an acetamidomethyl (Acm) protective group on the cysteine sulphur moiety. The substrate is treated with a solution of Iodine in ethanol, which deprotects the cysteine and forms oxidatively the disulphide bridge.

The reaction is performed using a setup as shown in FIG. 1. A summary of the components within each of the parts of the setup at the beginning of the process is provided in Table 3. A substrate feed solution (an acetic acid solution of about 18 mM or 22.5 g/L (1-9)NH$_2$DDAVP) is provided in a substrate feed tank (1). A iodine solution in ethanol (iodine concentration of about 200 mM or 25 g/L) is provided in a separate feed tank (2). The substrate feed solution and iodine solution are added continuously and simultaneously to the reactor (3) via first (7) and second (8) reactor inlets, respectively. The reactor (3) initially comprises a water—acetic acid mixture, to form a dilute reaction mixture comprising 1 g/L (1-9)NH$_2$DDAVP. The temperature inside the reactor (3) is about 26° C. As the reaction proceeds, reaction mixture is removed continuously from the reactor (3) via a reactor outlet (13) and entered to a filtration loop feed tank (4) via a filtration loop feed tank inlet (10). The filtration loop feed tank (4) initially only contains water. The solution contained in the filtration loop feed tank (4) is subjected continuously to constant volume diafiltration over a filtration membrane (5) having a retentate side (15) and a permeate side (16), using the solution in the reactor (3) as the diafiltration solution. The retentate (comprising 1-desamino-8-D-arginine) is returned to the filtration loop feed tank (4), whereas the permeate (solvent) is returned to the reactor (3) via a third reactor inlet (9). The permeate addition rate to the reactor (3) is matched with the substrate feed addition, such that a constant dilution of the substrate in the reactor (3) is obtained.

In practice, it is sufficient to measure the membrane flux for the first 200 mL of permeate. Based on the measured flux, the rate at which the substrate feed and iodine solution are added can be determined.

A 50 cm single tube 0.9 nm TiO$_2$ ceramic membrane (commercially available from Inopor, Germany) having a molecular weight cut off of about 450 Da is used as a filtration membrane. Rejection of the linear peptide starting material and the cyclic peptide product over the ceramic membrane used were both found to be about 97.5. The high rejection leads to an accumulation of the product 1-desamino-8-D-arginine in the filtration loop feed tank (4) as the reaction proceeds.

Membrane permeability was 0.6 lm$^{-2}$ hr$^{-1}$ bar$^{-1}$ for all experiments carried out with the membrane. Once the reaction was complete the diafiltration process was continued to ensure all reaction components had been transferred into the filtration loop. More particularly, the diafiltration process was allowed to run until 4 diafiltration volumes were passed over the membrane. It is expected that a shorter continuation of the diafiltration process would also provide good results.

Reduction of the time for the complete process can be achieved by increasing the membrane surface area, which increases the volume of permeate produced per hour and concomitantly the rate of reagent addition.

The results using this process (Experiment 1) are summarized in Table 4. The 1-desamino-8-D-arginine yield and (1-9)NH$_2$DDAVP conversion (as determined via ultra performance liquid chromatography—UPLC) was found to be comparable to the values obtained from a corresponding batch reaction (Experiment 2).

TABLE 3

Overview of the initial components within each part of the setup

| Setup part | Component | Mass (g) | Volume (ml) |
|---|---|---|---|
| Substrate feed tank (1) | (1-9)NH$_2$DDAVP | 4.0 | — |
|  | Acetic acid | 186.5 | 177.8 |
| Feed tank (2) | iodine | 1.22 | — |
|  | ethanol | 37.6 | 47.7 |
| Reactor (3) | Water | 267 | 267 |
|  | Acetic acid | 34.6 | 33 |
| Filtration loop feed tank (4) | Water | 400 | 400 |

TABLE 4

Summary of experimental results

| Experiment | 1 | 2 (batch reaction) | 3 |
|---|---|---|---|
| Yield (%) | 66.9 | 70.6 | 78.8 |
| Conversion (%) | 75.3 | 83.9 | 90.6 |
| Yield/conversion | 88.8 | 84.1 | 87 |
| Volume solvent used (ml) | 926 | 1135 | 934 |
| Volume solvent required for batch | 3588 | 1135 | 3588 |
| % reduction in solvent use | 74 | 0 | 74 |
| PMI | 473 | 1703 | 401 |

However, the processes described herein require considerably less solvent than the corresponding batch processes, as indicated by the PMI obtained for each experiments (Table 2). Indeed, it is clear that the PMI for the present processes is far lower than the PMI for the batch process, and allow for a reduction in solvent use of more than 70%. It is noted that the reaction could be optimized further (yield and conversion could be improved) by also providing some iodine to the reactor (3) at the start of the reaction, in addition to the iodine in the feed tank (2) (See Table 2, Experiment 3).

Thus, the processes described herein allow for carrying out reactions using similar substrate concentrations as in conventional batch processes, which results in a similar yield and purity of the obtained products. However, because the solvent is recycled continuously, the reactor (3) volume and the total amount of solvent required can be reduced significantly.

What is claimed is:

1. A continuous process for carrying out a chemical reaction of a substrate in a diluted reaction mixture comprising a solvent, the process comprising the steps of:
   (a) simultaneously adding a substrate feed and a solvent for diluting said substrate feed to form a reaction mixture in a reactor; and causing said substrate to form a reaction product in said reaction mixture;

(b) discharging, from an outlet of the reactor, reaction mixture comprising reaction product and solvent to a filtration loop feed tank; discharging reaction mixture from an outlet of said filtration loop feed tank;

(c) conducting the reaction mixture discharged from the filtration loop feed tank to a filtration membrane, wherein the filtration membrane is permeable to the solvent and provided to be impermeable to the reaction product, thereby obtaining a permeate comprising solvent and a retentate comprising reaction product;

(d) recycling the permeate entirely for diluting said substrate feed in step (a); and (e) conducting the retentate from said filtration membrane entirely to the filtration loop feed tank.

2. The process according to claim 1, wherein said reaction is selected from the group consisting of a cyclization reaction, a polymerization reaction, an enzymatic reaction with substrate inhibition, an enzymatic reaction with product inhibition, a reaction with precipitation of the substrate or of a co-reactant, and combinations thereof.

3. The process according to claim 1, wherein said substrate feed and said solvent enter said reactor as separate streams which are mixed inside said reactor, and wherein step (d) comprises continuously returning solvent which permeates the filtration membrane to said reactor.

4. The process according to claim 1, wherein said substrate feed and said solvent are mixed in a mixing vessel to form a diluted substrate feed which is continuously discharged from said mixing vessel to said reactor, wherein step (d) comprises continuously returning solvent which permeates the filtration membrane to said mixing vessel.

5. The process according to claim 1, wherein the volume of solvent added in step (a) is at least 5 times the volume of substrate feed added in step (a).

6. The process according to claim 1, wherein step (a) further comprises mixing said substrate feed and solvent with one or more additional components selected from a catalyst and a co-reactant which is to be reacted with said substrate.

7. The process according to claim 6, wherein said substrate feed is continuously discharged from a substrate feed tank and said one or more additional components are continuously discharged from one or more feed tanks other than said substrate feed tank.

8. The process according to claim 6, wherein the filtration membrane rejects less than 10% of one or more components selected from said co-reactant, said catalyst, and one or more side products to the retentate.

9. The process according to claim 1, wherein at least 95% of the solvent added in step (a) is solvent from the permeate side of the filtration membrane.

10. The process according to claim 1, wherein said filtration membrane rejects at least 90% of the reaction product to the retentate.

11. The process according to claim 1, wherein said filtration membrane rejects at least 95% of the substrate to the retentate.

12. The process according to claim 1, wherein said filtration membrane is selected from the group consisting of a nanofiltration membrane, a microfiltration membrane, an ultrafiltration membrane, a reverse osmosis filtration membrane, and combinations thereof.

13. The process according to claim 1, wherein a flux through the filtration membrane is adjusted by adjusting one or more of: a membrane parameter and a filtration parameter, and wherein the discharge rate of the reaction mixture from the reactor or from the filtration loop feed tank and a rate of addition of the substrate are determined by the flux.

* * * * *